United States Patent [19]

Kurachi et al.

[11] Patent Number: 5,654,802
[45] Date of Patent: Aug. 5, 1997

[54] METHOD AND DEVICE FOR INSPECTING BAGS

[75] Inventors: Akira Kurachi; Eiji Bando, both of Tokyo, Japan

[73] Assignee: Oji Seitai Kaisha, Ltd., Tokyo, Japan

[21] Appl. No.: 627,133

[22] Filed: Apr. 3, 1996

[51] Int. Cl.⁶ .................................................. G01B 11/00
[52] U.S. Cl. ........................ 356/394; 356/376; 356/372
[58] Field of Search ............................. 356/394, 376, 356/372, 167, 567, 561

[56] References Cited

U.S. PATENT DOCUMENTS

| | | |
|---|---|---|
| 3,433,135 | 3/1969 | Lokey et al. . |
| 3,524,389 | 8/1970 | Stork . |
| 3,581,629 | 6/1971 | Wiendieck . |
| 3,583,296 | 6/1971 | Stork et al. . |
| 3,643,552 | 2/1972 | Stork .................................... 93/27 |
| 4,258,267 | 3/1981 | Feldkämper . |
| 4,645,339 | 2/1987 | Feldkämper . |
| 4,896,211 | 1/1990 | Hunt et al. . |

FOREIGN PATENT DOCUMENTS

| | | |
|---|---|---|
| 0 571 728 | 12/1983 | European Pat. Off. . |
| 28 05 212 | 8/1979 | Germany . |
| 28 07 842 | 8/1979 | Germany . |
| 54-126177 | 2/1979 | Japan . |
| 54-126177 | 10/1979 | Japan . |
| 62-59022 | 3/1987 | Japan . |
| 62-59022 | 12/1987 | Japan . |
| 2 289 941 | 12/1995 | United Kingdom . |

*Primary Examiner*—Frank G. Font
*Assistant Examiner*—Reginald A. Ratliff
*Attorney, Agent, or Firm*—Burns, Doane, Swecker & Mathis, L.L.P.

[57] ABSTRACT

A method for inspecting bags having folded and pasting bottoms. Light source is provided to irradiate a bottom of a moving bag with a light so that shadows appear along a shape of bottom folds. A CCD linear array image sensor takes an image of the bottom of the bag from the reflected light and delivers electric signal corresponding to the image. The electrical signal are processed to extract a shape of bottom folds based on the shadows on the irradiated bottom. The obtained outer profile is compared with a reference input of a good bag stored in a memory to emit an electric selection signal classifying whether it is a good product or a defective product.

5 Claims, 4 Drawing Sheets

METHOD AND DEVICE FOR INSPECTING BAGS

BACKGROUND OF THE INVENTION

1. Field of the Invention

The present invention relates to a method and a device for inspecting bags, and in particular, it relates to an improved method for inspecting whether bottoms of square bottom bags (called "SOS" bags) or hexagonal bottom bags (called "cross bottom bags") are exactly folded or not to detect (reject) defective products, and to a device for carrying out said method.

2. Description of the Related Art

Proposals have been made to inspect whether bottoms of bags are exactly folded or not by a SOS bag machines or hexagonal bottom forming machines (called "a cross bottomer" or simply "a bottomer"). For example, regarding hexagonal bottom bags, Japanese Examined Patent Publication (Kokoku) No. 62-59022 discloses a method for inspecting bags while bags are conveyed on a bottomer after the bottoms thereof are folded and closed. The bodies of the bags are arranged in a flat and horizontal position, and the spreaded or closed bottoms of the bags are arranged in a vertical position, i.e., perpendicular to the bag bodies. The bottom has a pair of upper and lower opposite sides and four remaining oblique sides. The bags are conveyed in transverse direction, i.e., the upright bottoms are parallel to the conveying direction. The inspecting device comprises four photoelectric cells; two cells are arranged just outside the upper and lower sides to normally emit a bright signal, and the remaining two cells are arranged just inside the upper and lower sides to emit a normally dark signal, so that the top and lower sides of the moving bottoms are scanned and it is judged whether the bottoms are exactly folded or not due to a detected parallelism of the upper and lower sides.

Japanese Unexamined Patent Publication (Kokai) No. 54-126177 also discloses a method for inspecting hexagonal bottom bags. The bags are conveyed on a bottomer in a similar manner to the above described case, so that the bags are conveyed in transverse direction, i.e., the upper and lower sides of the bottoms are parallel to the conveying direction. The inspecting device comprises four photoelectric cells and pulse encoders. According to this prior art, the length of the upper and lower sides of the bottom, the length from the leading end of the moving bottom (i.e. the apex of the leading triangle pocket) to the leading end of the upper and lower sides, and the length from the trailing end of the top and lower sides to the trailing end of the moving bottom (i.e. the apex of the trailing triangle pocket) are measured, and it is judged whether triangular pockets of the bottom are exactly folded at 45 degrees or not.

In addition, this publication also discloses to carry out the detection during a bottom forming process before the bottom of the bag is finally closed, i.e., just after the bottom end is spreaded. In this case too, the length of the top and lower sides of the bottoms, the length from the leading end of the bottom (i.e. the apex of the training triangle pocket) to the leading ends of the upper and lower sides, and the length from the trailing end of the top and lower sides, to the trailing end of the moving bottom (i.e. the apex of the trailing triangle pocket) so as to judge whether triangular pockets of the bottoms are exactly folded at 45 degrees or not.

However, these inspecting methods and devices can be applied only to the hexagonal bottom manufacturing machines in which the bags are conveyed in such a manner that the bottoms are arranged in a vertical position relative to the horizontal flat tube bodies and the bags are conveyed in transverse direction, but cannot be applied to the SOS bag machines in which the bags are conveyed in such a manner that the bags are conveyed in longitudinal direction with the bottoms directed on the leading side, since these inspecting methods and devices use photoelectric cells. That is, the bottom is overlapped with the bag body, so it is difficult to identify the contour of the bottoms with the use of photoelectric cells.

A further device for inspecting so-called SOS bags having square bottoms is shown in FIGS. 5A and 5B, in which detecting rollers 15 are arranged on a delivery cylinder 14 which is arranged in a SOS bag machine after a bottom closing station. Magnetic field type proximity switches 16 are arranged to cooperate with the detecting rollers 15. FIG. 6 shows a SOS bag 20 having a square bottom 21 comprising folded flaps 22 delimited by outer shape lines 23. The detecting rollers 15 are arranged so that they contact the portions A, B, C and D of the bottom 21. The thickness of the portions A, B, C and D of the bottom 21 differs from each other due to the difference in the overlapped paper layers. The proximity switches 16 detect the thickness of the portions A, B, C and D and it is judged whether the bottom 21 of the bag 20 is exactly folded or not by comparing the detected thickness and a predetermined value.

For example, the portions A and B are symmetrically arranged to each other and the portions C and D are symmetrically arranged to each other, with the portion C including a longitudinal seam 24. Accordingly, the portions A and B comprise 6 layers, the portion C comprises 14 layers, and the portion D comprises a 10 layers. If the bottom 21 is not exactly folded and a portion or the whole of the portions A, B, C, and D is shifted out of the detecting rollers 15, the detected thickness will not correspond to the predetermined values and the bag will be rejected by a rejection means.

In this SOS bag machine, there are problems in that an erroneous inspection occurs if the bags are caught not correctly (e.g. aslant) gripped by fingers on the delivery cylinder 14, that an erroneous detection occurs if the detecting rollers 15 jump depending on the urging pressure thereof, and that it is not possible to carry out the detection at positions where fingers or grooves are located on the delivery cylinder 14 and so it is not possible to carry out the inspection for some particular bag sizes.

The above described prior arts inspect whether the bottoms are exactly folded or not by detecting or measuring the position, the dimension or the thickness of a particular portion or portions of the bottoms of the bags, based on the assumption that the folding lines or the outer shape lines of the flaps are straight irrespective of the fact that the bottoms are exactly folded or not. According to these prior arts, an erroneous inspection may occur if the bottom fold lines or the outer shape lines of the flaps are curved or the flaps are wrinkled. Also, it is not possible to detect any break in the flaps which may occur during folding the flaps.

SUMMARY OF THE INVENTION

The object of the present invention is to provide a method and a device for detecting bags having defective bottoms, which can be applied for SOS bag machines and hexagonal bottom forming machines and by which it is possible to identify an entire contour of the flaps of the bottoms to detect whether the bottoms are exactly folded or not.

According to the present invention, there is provided a method for inspecting bags having folded and pasted bottoms. The method comprises the steps of irradiating a bottom of a moving bag with light after spread or closure of a bottom end of a bag in a bag manufacturing process so that shadow lines appear along the bottom folds of the bag, receiving brightness and darkness of the light reflected by the bottom of the bag to take an image of the bottom folds of the bag and to convert the image into electrical binary signals using a CCD linear array image sensor, processing the electrical (binary) signals to extract shape of said bottom folds, and comparing the obtained shape of said bottom folds with a reference input of a good bag stored in memory means to emit an electric selection signal.

The present invention also provides a device for inspecting bags having folded and pasted bottoms. The device comprises light source for irradiating a bottom of a moving bag with a light after spread or closure of a bottom end of a bag in a bag manufacturing process so that a shadows appear along bottom folds of the bag, a CCD linear array image sensor for receiving brightness and darkness of the light reflected by the bottom of the bag to take an image of the bottom folds of the bag and to convert the image into electrical binary signals, memory means for storing a reference input of a good bag, and signal processing means for processing the electrical (binary) signal delivered from the CCD linear array image sensor to extract a shape of said bottom folds, and for comparing the obtained shape of said bottom folds with a reference input of a good bag stored in the memory means to emit an electric selection signal classifying whether it is a good product or a defective product.

With this arrangement, it is possible to extract a shape of the bottom folds for comparing the obtained shape of the bottom folds with a reference input of a good bag, in a manner quite different from the prior arts which detect the position, the dimension or the thickness of a particular portion or portions of the bottoms of the bags to judge whether the bottoms are exactly folded or not. Therefore, it is possible to exactly know whether the bottoms are exactly folded or not, including an occurrence of any break and wrinkles in the bottoms during the bottom folding, regardless of the conveying position and the direction of the bags.

It is possible to use a high frequency fluorescent lamp as a light source for irradiating the bottom of the bag. The fluorescent lamp extends perpendicular to the conveying direction of the bags, and a position sensor such as a linear beam sensor can be arranged for detecting an arrival of a leading end of the moving bag at a predetermined position. The position sensor cooperates with the moving means for moving the bags to emit a moving signal. For example, a travelling distance measuring means such as a pulse encoder is arranged for measuring the distance between the leading end of the moving bag and the light reflecting point. Therefore, it is possible to take the image of the bottom of the bag, especially appearing in the form of a brightness and a darkness along the bottom folds of the bag, at a constant pitch along the conveying direction, and in a continuous line along the transverse direction, perpendicular to the conveying direction.

It is preferable that the electrical (binary) signals delivered from the CCD linear array image sensor is processed to extract the shape of the bottom folds in the processing device as a video signal, and preferably a digital signal.

BRIEF DESCRIPTION OF THE DRAWINGS

The present invention will become more apparent from the following description of the preferred embodiments, with reference to the accompanying drawings, in which.

DESCRIPTION OF THE PREFERRED EMBODIMENTS

Figure 1:
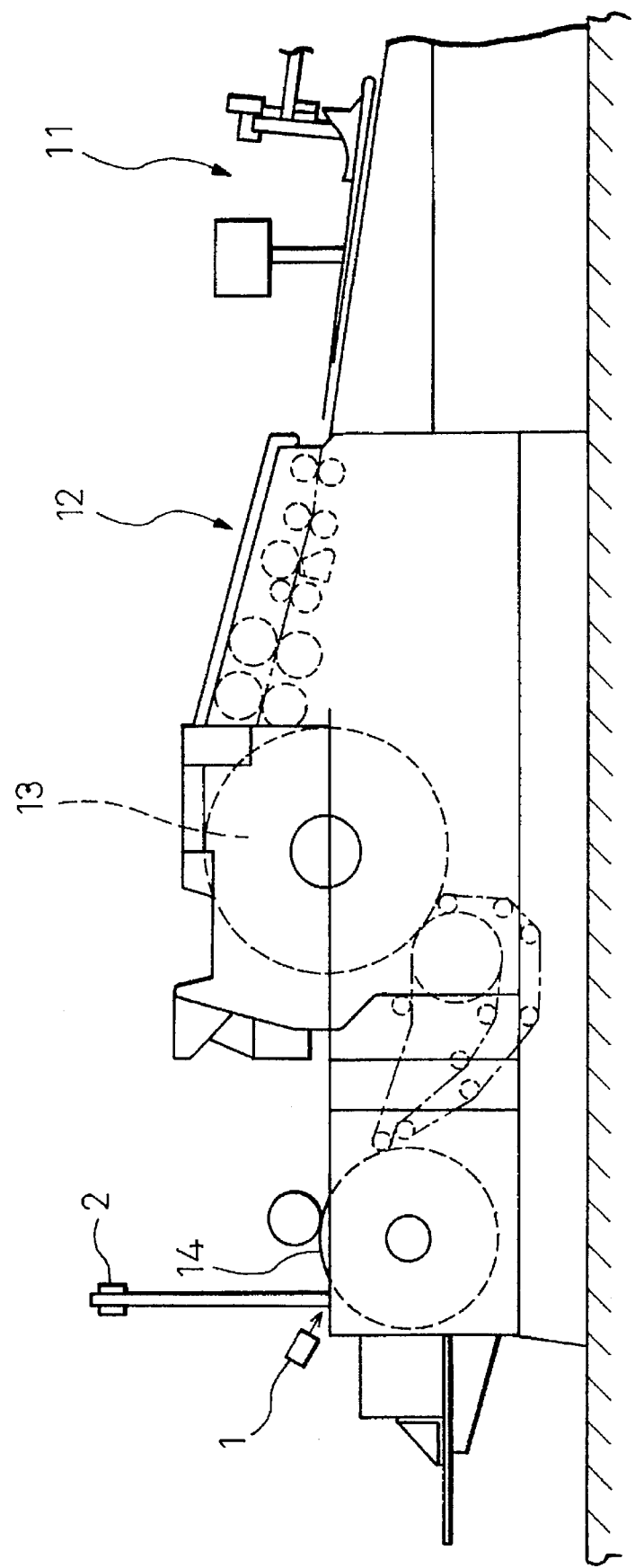
FIG. 1 is a side elevational view of a square bottom bag manufacturing machine according to the embodiment of the present invention.
Figure 2:
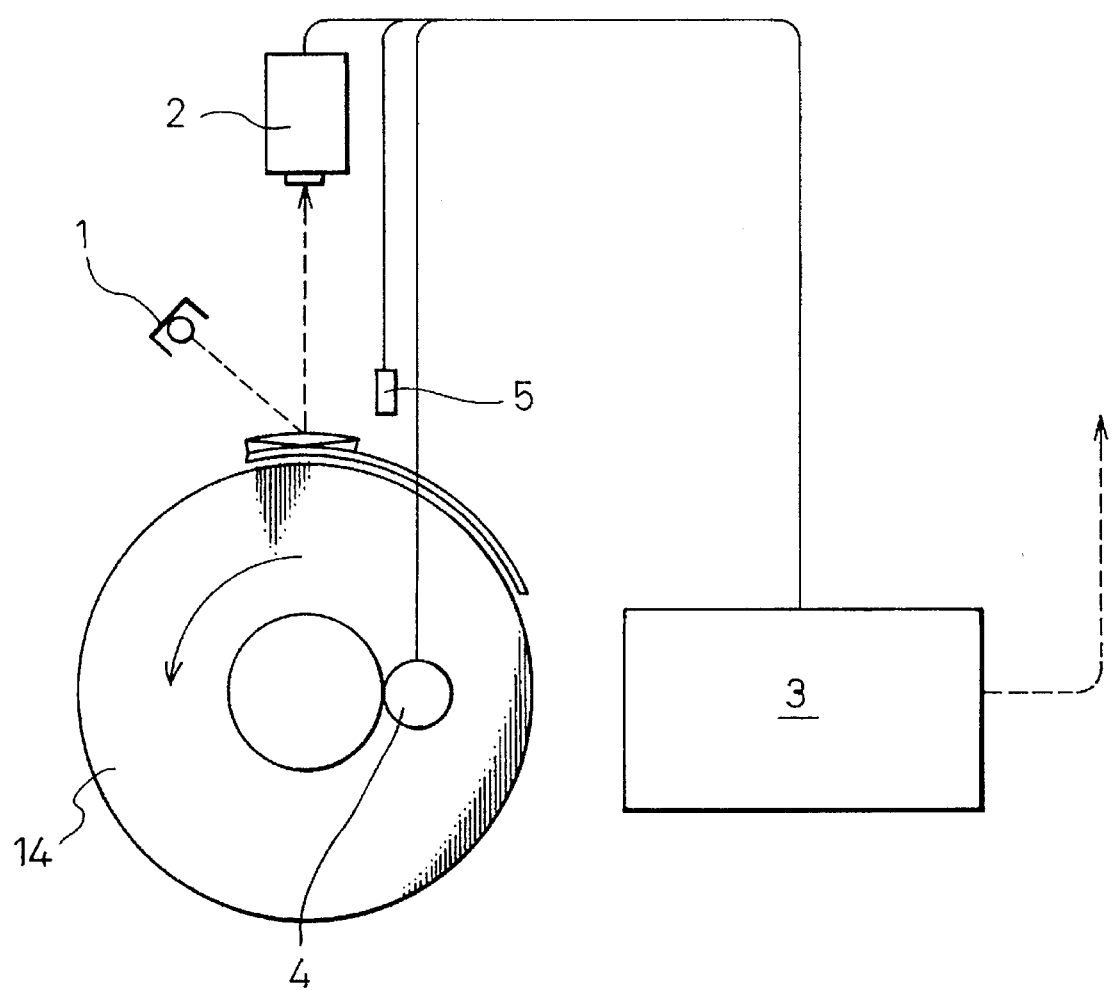
FIG. 2 is an enlarged view of a portion of the machine of FIG. 1.

FIG. 1 is a side elevational view of a SOS bag machine according to the embodiment of the present invention, and FIG. 2 is an enlarged view of a portion of the machine of FIG. 1. The reference numeral 1 denotes a light source, the reference numeral 2 denotes a light receiver, the reference numeral 3 denotes a signal processing device, the reference numeral 4 denotes a pulse encoder, and the reference numeral 5 denotes a linear beam sensor. The SOS bag machine includes a tubing station 11 for forming a continuous tube from a continuous paper web, a cutting station 12 for cutting the continuous tube into pieces of tubular segments, a bottom forming cylinder 13 for forming a bag with a closed bottom, and a delivery cylinder 14. The bottom forming operation includes an end spreading (a first folding) step and an end closing (a second folding) step, as is well known in the art.

Figure 3:
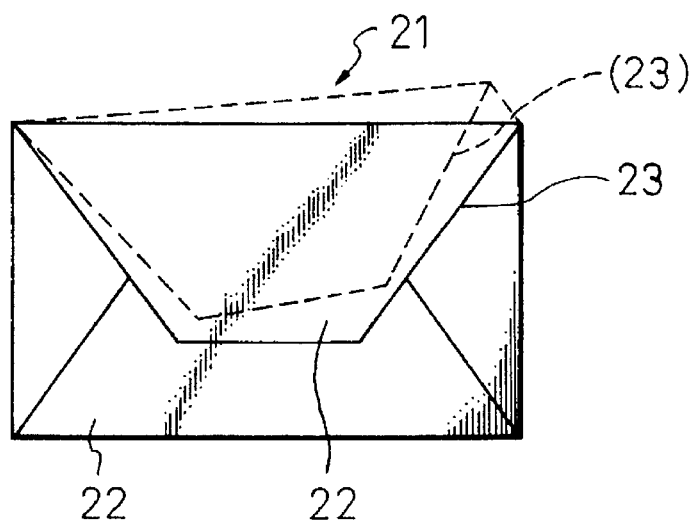
FIG. 3 is a view illustrating the bottom of the bag.
Figure 4:
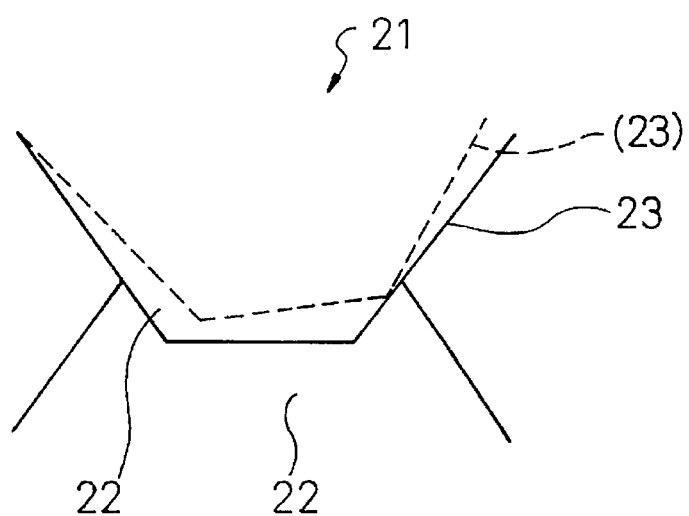
FIG. 4 is a view similar to FIG. 3, but illustrating another form of a detected contour of the flaps.
Figure 5A:
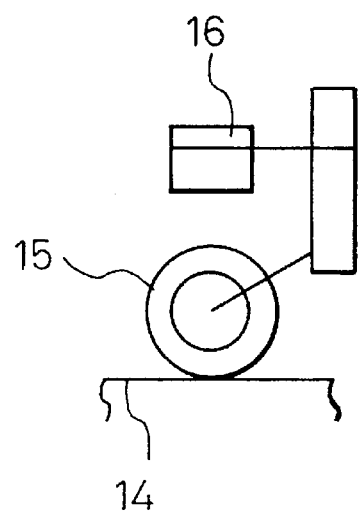
FIGS. 5A and 5B are views illustrating a prior art.
Figure 5B:
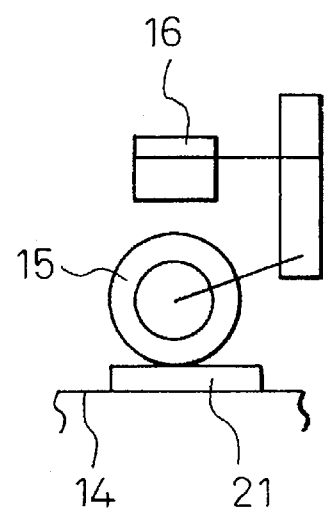
Figure 6:
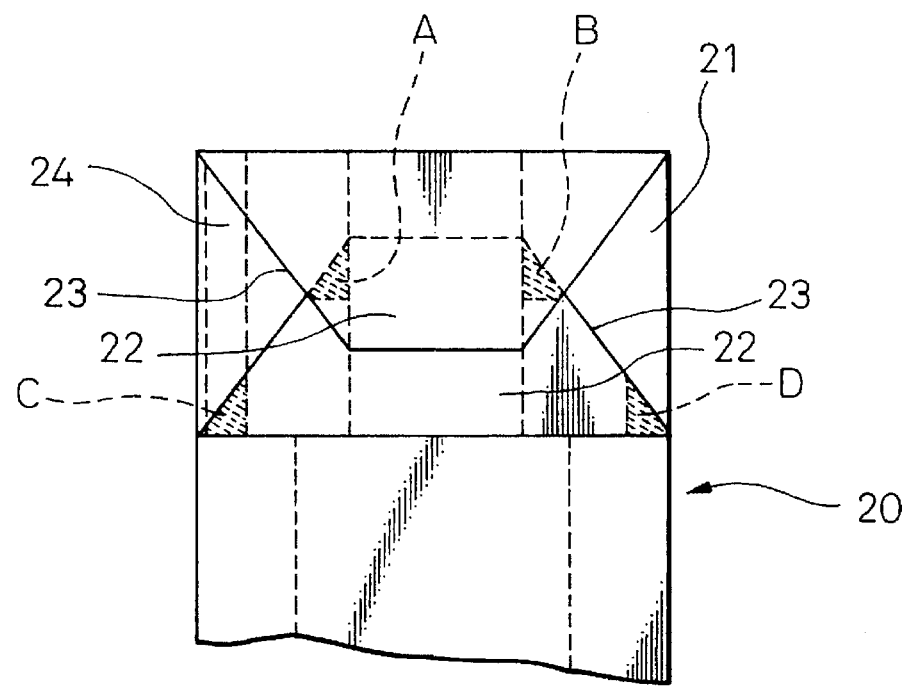
FIG. 6 is a plan view of a square bottom bag, illustrating the method for detecting defective bags of the prior art.

The SOS bag 20 has a square bottom 21 comprising folded flaps 22 delimited by outer shape lines or folding lines 23, as shown in FIG. 6. The bottom 6 of the SOS bag 20 is also shown in FIGS. 3 and 4.

The device for inspecting the bags is arranged on or near the delivery cylinder 14. The light source 1 comprises a high frequency fluorescent lamp of about 30 kilohertz. The light source 1 is arranged above the delivery cylinder 14 and extends in the widthwise direction of the delivery cylinder 14, so that the bottom 21 of the SOS bag 20, which is secured and conveyed by fingers (not shown) belonging to the delivery cylinder 14, is irradiated with the light over the entire width thereof so that shadows appear along the bottom folds i.e. the outer shape line 23 of the flaps 22 of the bottom 21.

The light receiver 2 comprises a CCD (charge coupled device) linear array image sensor arranged in a line which receives brightness and darkness of the light reflected by the bottom 21 of the bag 20 to take an image of the bottom folds of the bag over a full width of the bottom and to convert the image into an electrical binary signal (video signal).

The linear beam sensor 5 normally measures the distance between the linear beam sensor 5 and the delivery cylinder 14, and emits a signal when the leading end of the bag 20 gripped by fingers of the delivery cylinder 14 has just passed below the linear beam sensor 5 and a distance being measured is suddenly reduced. Receiving said signal, the pulse encoder 4 starts to measure the positional information of the bottom 21 of the bag in the conveying direction to thereby measure the moving distance of the bottom. This enables the light receiver 2 to take images intermittently in the conveying direction.

The signal processing device 3 processes the electrical signal (video signal) from the light receiver 2, the leading end detecting signal from the linear beam sensor 5, and the distance signal from the pulse encoder 4, to extract the shape of the bottom folds by digitizing the video signal from the light receiver 2 into binary signals. The signal processing device 3 has a comparator contained therein and compares the obtained shape of the bottom folds with a reference input of a good bag stored in the comparator to emit an electric selection signal classifying whether it is a good product or a defective product. For example, if the obtained shape of the bottom folds correspond to those shown by the solid line 22 in FIG. 3, an electric selection signal indicating a good product is delivered. If the obtained shape of the bottom folds correspond to those shown by the broken line 22 in FIG. 3, an electric selection signal indicating a defective product is delivered. Then, the defective product is rejected from the row of good products by an appropriate rejecting means.

The signal processing for extracting the shape of the bottom folds can be carried out by video signal or binary signal, the latter processing being stable and preferable. As a sensor for detecting the leading end of the moving bag, it is preferable to use the linear beam sensor 5 which detects the distance (i.e., the thickness of a bag), as illustrated in the embodiment, since a reflection type photoelectric switch reacts with a printing on the bag.

It is preferable to detect the shape of the bottom folds including the outer contour of the bottom, as shown in FIG. 3, by which it is also possible detect any break in the paper of the bag. However, it is possible to extract only the shape of the bottom folds i.e. the outer shape line of the flaps of the bottom, without including the outer contour of the bottom, as shown in FIG. 4.

It is to be understood that the method and the device for inspecting bags having folded and pasted bottoms can be applied to a hexagonal bottom forming machine to detect any deficiency of the bottoms of the hexagonal bottom bags.

As explained, according to the present invention, it is possible to extract a shape of the bottom folds and for comparing the obtained shape of the bottom folds with a reference input of a good bag, and it is possible to exactly know whether the bottoms are exactly folded or not, including an occurrence of any break and wrinkles in the bottoms during a bottom spreading process or a bottom closing process, regardless of the conveying position and the direction of the bags.

Since the image of the bottom of the bag is taken in line and the total image is realized in the processing device to compare the image with a reference input, it is possible to arrange the light source and the light receiver in a relatively narrow area.

The present invention can be applied both of the SOS bag machine and the hexagonal bottom forming machine, and provides for a reliable method and device for detecting defective bags by taking into account the entire shape of the bottom folds of the bags to judge whether the bottoms are exactly folded or not.

What is claimed is:

1. A method for inspecting bags having folded and pasted bottoms, said method comprising the steps of:

irradiating a bottom of a moving bag with light after spread or closure of a bottom end of a bag in a bag manufacturing process so that shadow lines appear along bottom folds of the bag, the bottom folds being delineated by edge lines;

receiving the light reflected by the bottom of the bag to take an image of the bottom folds of the bag over a full width of the bottom and to convert the image into electrical signals, using a CCD linear array image sensor;

measuring the distance between a leading end of the bag and a point at which light is reflected from the bag;

processing the electrical signals to obtain a shape of said bottom folds; and comparing the obtained shape of said bottom folds with a reference input of a good bag stored in memory means to emit an electric selection signal classifying whether it is a good bag or a defective bag.

2. A device for inspecting bags having folded and pasted bottoms, said device comprising:

a light source for irradiating a bottom of a moving bag with a light after spread or closure of a bottom end of a bag in a bag manufacturing process so that shadows appear along bottom folds of the bag, the bottom folds being delineated by edge lines;

a CCD linear array image sensor for receiving the light reflected by the bottom of the bag to take an image of the bottom folds of the bag over a full width of the bottom and to convert the image into electrical signals;

travelling distance measuring means for measuring the distance between a leading end of the bag and a light reflecting point at which light is reflected from the bag;

memory means for storing a reference input of a good bag; and signal processing means for processing the electrical signals delivered from the CCD linear array image sensor to extract a shape of said bottom folds, and for comparing the obtained shape of said bottom folds with a reference input of a good bag stored in said memory means to emit an electric selection signal classifying whether it is a good bag or a defective bag.

3. A device according to claim 2, further comprising a position sensor for detecting arrival of the leading end of the moving bag at a position relative to the light reflecting point between incident light from the light source and the light reflected to the CCD linear array image sensor.

4. A device according to claim 3, wherein the position sensor comprises a linear beam sensor.

5. A device according to claim 2, wherein said travelling distance measuring means comprises a pulse encoder.

* * * * *